US010894081B2

(12) United States Patent
Zheng et al.

(10) Patent No.: US 10,894,081 B2
(45) Date of Patent: Jan. 19, 2021

(54) RECOMBINANT BIVALENT INACTIVATED VACCINE AGAINST FOOT-AND-MOUTH DISEASE VIRUS, PREPARATION METHOD AND USE THEREOF

(71) Applicant: Lanzhou Veterinary Research Institute Chinese Academy of Agricultural Sciences, Gansu (CN)

(72) Inventors: Haixue Zheng, Gansu (CN); Fan Yang, Gansu (CN); Zixiang Zhu, Gansu (CN); Weijun Cao, Gansu (CN); Hong Tian, Gansu (CN); Keshan Zhang, Gansu (CN); Dan Li, Gansu (CN); Ye Jin, Gansu (CN); Jianhong Guo, Gansu (CN); Jijun He, Gansu (CN); Xuepeng Cai, Gansu (CN); Xiangtao Liu, Gansu (CN)

(73) Assignee: LANZHOU VETERINARY RESEARCH INSTITUTE CHINESE ACADEMY OF AGRICULTURAL SCIENCES, Gansu (CN)

( * ) Notice: Subject to any disclaimer, the term of this patent is extended or adjusted under 35 U.S.C. 154(b) by 0 days.

(21) Appl. No.: 16/346,496

(22) PCT Filed: Mar. 23, 2018

(86) PCT No.: PCT/CN2018/080244

§ 371 (c)(1),
(2) Date: Apr. 30, 2019

(87) PCT Pub. No.: WO2018/192338

PCT Pub. Date: Oct. 25, 2018

(65) Prior Publication Data

US 2020/0237897 A1 Jul. 30, 2020

(30) Foreign Application Priority Data

Apr. 19, 2017 (CN) .......................... 2017 1 0256450

(51) Int. Cl.

| | |
|---|---|
| ***A61K 39/135*** | (2006.01) |
| ***C12N 7/00*** | (2006.01) |
| *A61K 39/00* | (2006.01) |

(52) U.S. Cl.
CPC .............. *A61K 39/135* (2013.01); *C12N 7/00* (2013.01); *A61K 2039/5252* (2013.01); *A61K 2039/552* (2013.01); *A61K 2039/55566* (2013.01); *A61K 2039/57* (2013.01); *A61K 2039/70* (2013.01); *C12N 2770/32121* (2013.01); *C12N 2770/32134* (2013.01); *C12N 2770/32171* (2013.01)

(58) Field of Classification Search
None
See application file for complete search history.

(56) References Cited

FOREIGN PATENT DOCUMENTS

| | | | |
|---|---|---|---|
| CN | 1541710 | A | 11/2004 |
| CN | 103266091 | A | 8/2013 |
| CN | 107029231 | A | 8/2017 |

OTHER PUBLICATIONS

Bai et al. (Virology Journal. 2010; 7: 2008).*
Zheng et al. (PLOS ONE; Jan. 2013; 8 (1): e55228).*
International Search Report for PCT Application No. PCT/CN2018/080244 dated May 23, 2018; 2 pgs.
Yi, Jianzhong, et al., “Recombinant Bivalent Vaccine against Foot-and-Mouth Disease Virus Serotype O/A Infection in Guinea Pig,” Acta Biochimica et Biophysica Sinica; Dec. 31, 2004; 36(9):589-596.

* cited by examiner

*Primary Examiner* — Shannon A. Foley
(74) *Attorney, Agent, or Firm* — Umberg Zipser LLP

(57) ABSTRACT

The present disclosure relates to a foot-and-mouth disease virus vaccine composition, especially a recombinant bivalent vaccine composition against type O and type A foot-and-mouth disease viruses. The present disclosure further relates to a method for preparing the foot-and-mouth disease virus vaccine composition, and a use of the foot-and-mouth disease virus vaccine composition in preparing medicines for preventing and/or controlling foot-and-mouth disease in animals.

14 Claims, 3 Drawing Sheets

Specification includes a Sequence Listing.

SEQUENCE LISTING

```
<160> NUMBER OF SEQ ID NOS: 7

<210> SEQ ID NO 1
<211> LENGTH: 3591
<212> TYPE: DNA
<213> ORGANISM: Foot-and-mouth disease virus

<400> SEQUENCE: 1

cttaagggac aggaacacgc cgtgtttgcc tgcgtcacct ccaacgggtg gtacgcgatc      60
gacgacgaag aattctaccc ctggacgcca gatccgtccg acgtgctggt ctttgtcccg     120
tacgatcaag aaccacttaa tggagaatgg aaagcaaggg ttcagagacg gctcaaggga     180
gccggacaat ccagtccggc tactgggtca cagaaccaat caggcaacac cgggagtatc     240
atcaacaatt actacatgca gcaataccag aactccatgg acacccaact tggtgacaat     300
gctatcagcg gaggctccaa cgagggatcc acagacacaa cctccaccca cacaaccaac     360
actcagaaca atgactggtt ttcaaagttg gccagctctg ccttcagcgg tcttttcggc     420
gccctcctcg ccgataagaa aaccgaggag accactcttc tcgaggaccg catcctcacc     480
acccgaaacg gacacaccac ctcgacaacc cagtcgagtg ttggcataac gcacgggtac     540
gcaacagctg aggattttgt gaacgggcca aacacctctg gtcttgagac cagagttgtc     600
caggcggaac ggttctttaa aacccacctg ttcgactggg tcaccagtga tccgttcgga     660
cggtactact tgttggagct cccgactgac cacaaaggtg tctacggcag cctgaccgac     720
tcatacgcct acatgagaaa cggttgggat gttgaggtca ccgctgtggg gaatcagttc     780
aacggaggct gcctactggt ggccatggta cctgaacttt gttccatcga gcggagagag     840
ctgttccagc ttacgctctt cccccaccag ttcatcaacc cccggacgaa catgacagcc     900
cacatcaagg tgccctttgt tggcgtcaac cgttacgatc agtacaaggt acacaagccg     960
tggaccccttg tggttatggt cgtagcccca ctgactgtca acaccgaagg cgctccgcag    1020
atcaaggtgt atgccaacat cgcacccacc aacgtgcacg tcgcgggtga gttcccttcc    1080
aaagagggga ttttccctgt ggcctgtagc gacggttatg gcggcttggt gacaactgac    1140
ccaaagacgg ctgaccccgt ttacggcaaa gtgttcaacc ccccccgcaa catgttgccg    1200
gggcggttca ccaacctcct gggcgtggct gaggcttgcc ccacgtttct gcacttcgat    1260
ggtgacgtac cgtatgtgac cactaagacg gattcggaca gggtgctcgc acaatttgac    1320
ttgtctttgg cagcaaaaca catgtcaaac accttccttg caggtcttgc ccagtactac    1380
acgcagtaca gcggcaccgt taacctgcac ttcatgttca caggtcccac tgacgcgaaa    1440
gcgcgttaca tgattgcgta tgcccctccg ggcatggagc cgcccaaaac acctgaggct    1500
gctgctcact gcattcacgc agagtgggac acgggtctga actcaaagtt taccttttcc    1560
atcccctacc tctcggcggc tgattacgcg tacaccgcgt ctgacgctgc tgagaccaca    1620
aatgttcagg gatgggtctg cttatttcaa ataacacacg ggaaagctga gggtgacgct    1680
cttgtcgtgc tggccagtgc tggcaaagac tttgagctgc gcctgcctgt ggacgctcgg    1740
```

```
caacagacca cttcgacggg cgagtcggct gaccccgtga ctgccaccgt tgagaattac   1800
ggtggcgaga cacaggtcca gaggcgccac cacacagacg tctcattcat attggacaga   1860
tttgtgaaag tcacaccaaa agactcaata aatgtattgg acctgatgca gaccccctcc   1920
cacaccctag taggggcgct cctccgcact gccacttact atttcgctga tctagaggtg   1980
gcagtgaaac acaaggggga ccttacctgg gtgccaaatg gagcacctga agcagccttg   2040
gacaacacca ccaacccaac ggcgtactat aaggcgccgc ttacccggct tgcattgccc   2100
tacacggcac cacaccgtgt tttggccacc gtttacaacg ggaaatgcaa atacgccggg   2160
ggctcactgc ccaacgtgag aggcgatctc caagagctgg ctcagaaggc agcgaggccg   2220
ctgcctactt ctttcaacta cggtgccatc aaagccactc gggtgacaga actgctgtac   2280
cgcatgaaga gggccgagac gtactgtcct cggccccttt tggctgttca cccgagtgcg   2340
gccagacaca aacagaaaat agtggcgcct gtaaagcagt ccttgaactt tgatctgctc   2400
aagttggcag gggacgtgga gtccaaccct gggcccttct tcttctctga cgtcaggtca   2460
aacttcacca aactggtgga aaccatcaac cagatgcaag aggacatgtc aacaaaacac   2520
ggacccgact ttaaccggtt ggtatcagcg tttgaggaat tggccgctgg ggtgaaagcc   2580
atcaggaccg gcctcgacga ggccaaaccc tggtacaagc tcatcaagct cctgagccgc   2640
ttgtcatgca tggccgctgt agcagcacgg tccaaggacc cagtccttgt ggctatcatg   2700
ctggctgaca ccggtcttga gattctggac agcacatttg tcgtgcagaa aatctccgac   2760
tccctctcca gtctctttca cgtgccggcc cccgtcttca gtttcggagc tccgattctg   2820
ctagccgggt tggtcaaggt cgcctcgagc ttcttccggt ccacacccga ggatctcgag   2880
agagcagaga aacagctcaa agcacgtgac atcaatgaca tcttcgccat tctcaagaac   2940
ggcgagtggc tggtcaagtt gatcctagcc atccgcgact ggattaaagc atggatcgcc   3000
tcagaagaga agtttgtcac catgacagac ttggtgcctg gcatccttga aaagcagcgg   3060
gacctcaacg acccggccaa gtacaaggaa gccaaggaat ggctcgacaa cgcgcgccaa   3120
acgtgtttga agagcgggaa cgtccacatt gccaacctgt gcaaagtggt cgccccagca   3180
ccgagcaagt cgagacctga acccgtggtc gtgtgcctcc gcggcaaatc cggtcagggt   3240
aagagtttcc ttgcgaacgt gctggcacaa gccatctcta cccactttac cggcaggact   3300
gactcagttt ggtactgtcc gccagaccct gaccacttcg acggttacaa ccagcagacc   3360
gttgttgtga tggatgattt gggccagaat cccgacggca aggacttcaa gtacttcgcc   3420
cagatggtct cgaccacggg gttcatcccg cccatggctt cacttgagga caaaggcaag   3480
cctttcaaca gcaaagtcat cattgccacc accaacctgt actcgggctt caccccgaga   3540
accatggtgt gccccgatgc gctgaaccga aggtttcact ttgacatcga t            3591
```

<210> SEQ ID NO 2
<211> LENGTH: 40
<212> TYPE: DNA
<213> ORGANISM: Artificial Sequence
<220> FEATURE:
<223> OTHER INFORMATION: OP12A-F

<400> SEQUENCE: 2

```
ttttccttaa gggacaggaa cacgccgtgt ttgcctgcgt                           40
```

<210> SEQ ID NO 3
<211> LENGTH: 29
<212> TYPE: DNA

<213> ORGANISM: Artificial Sequence
<220> FEATURE:
<223> OTHER INFORMATION: OP12A-R

<400> SEQUENCE: 3
actcacatcg atgtcaaagt gaaaccttc 29

<210> SEQ ID NO 4
<211> LENGTH: 2373
<212> TYPE: DNA
<213> ORGANISM: Foot-and-mouth disease virus

<400> SEQUENCE: 4
cttaagggac aggaacacgc agtgtttgcc tgtgttacct ccaacgggtg gtacgcgatt 60
gacgacgagg acttttaccc ctggacacca gacccgtctg atgtcctggt gtttgtcccg 120
tatgatcaag aaccactcaa cggagaatgg aaaacaaagg ttcagaggcg acttaaaggg 180
gcagggcaat ctagccccgc caccgggtcg cagaaccagt caggcaatac cggcagcatc 240
attaacaact actacatgca gcagtaccag aactccatgg acacacaact tggtgacaac 300
gccatcagcg gaggatccaa cgaggggtcc acggacacaa cctctaccca cacaaccaac 360
acccaaaaca atgactggtt ctcaaaactg gcaagttctg cattcaccgg tcttttcggc 420
gcactgctcg ccgacaagaa gaccgaagag acaactcttc tggaggaccg tatcctcacc 480
actcgtaatg gacacaccac ctctacaact cagtcgagtg tgggggtcac ctacgggtat 540
tcaactggtg aggaccacgt ttctggacct aacacatcag gtttggagac gcgggtggta 600
caagctgaaa ggttcttcaa gaagcacttg tttgattgga caacggacaa accctttggt 660
cacattgaaa agctggaact tcccactgat cacaaaggtg tctacggaca gctggtggac 720
tcctttgcat acatgagaaa tggctgggac gtggaggtgt ctgctgttgg caaccagttc 780
aacggcgggt gccttctcgt ggccatggta cctgagttta aggagttcac cacacgtgaa 840
aagtaccagc tcaccctgtt cccccaccag ttcattagcc ccagaaccaa catgaccgcg 900
cacatcacgg tcccgtacct tggtgtgaac aggtatgacc agtacaacaa acacaaaccc 960
tggacgttgg tggtgatggt ggtttcgcca cttaccacta gctccattgg tgcatcacag 1020
attaaggtct acaccaacat cgccccgacc cacgttcacg tggctggcga gctcccgtcg 1080
aaagagggga tcgtgccagt cgcctgctcg gacgggtacg gtggcctggt gacaacagac 1140
cctaaaacag ctgaccctgc ttacggtatg gtgtacaacc cacctaggac caactacccc 1200
gggcggttta caaacttgtt ggacgtggca gaggcgtgcc ccaccttcct ctgtttcgac 1260
gacgggaaac cgtacgttgt gacaagaacg gacgagcagc gcctcttggc caagtttgac 1320
ctttcccttg ctgcaaagca catgtcaaac acctaccttt cagggatagc acagtactac 1380
gcacagtact ctggcaccat caatttgcac ttcatgttta ctggttccac tgactcaaag 1440
gcccgttaca tggtggctta cgtcccgccc ggcgtgacaa cgccaccgga cacgcctgag 1500
agagctgcgc actgcatcca cgcagaatgg gacacggggc taaactccaa attcactttt 1560
tcaatcccat acgtatctgc tgcagattac gcgtacacag cgtccgatgt ggcagacaca 1620
acaaacgtac agggatgggt ttgcatctac caaatcaccc atgggaaggc cgaacaagac 1680
actctggttg tgtcggtcag cgccggcaaa gactttgagc tgcgcctccc cattgacccc 1740
cgtgcgcaaa ccaccgccac cggggaatca gcagaccccg tcacaaccac cgtcgagaac 1800
tacggtggtg agacacaagt gcagcgacgc caccacaccg acgtcagctt cataatggac 1860
aggtttgtgc aaatcaagcc tgtgagcccc acacatgtca ttgacctcat gcaaacacac 1920

-continued

```
caacacgggc tggtgggcgc tatgttgcgc gcggccacct actacttttc tgatcttgag   1980

attgtggtga accacacggg tcgcctaacg tgggtaccca atggagcacc tgaggcagca   2040

ctggacaaca cgagcaaccc cactgcttac cacaaagcac cgttcacacg gcttgcactc   2100

ccttacaccg cgccacaccg cgtgttggca actgtgtaca acgggaatag caagtactct   2160

gcgcctgcaa cacggcgagg tgacttgggg tctctcgcgg cgaggctcgc cgcacagctt   2220

cctgcctcct tcaactacgg cgcgattcga gccacggaga tccaagaact cctcgtgcgc   2280

atgaagcgtg ccgagctcta ctgccccagg ccactgctgg cggtggaggt gacgtcacaa   2340

gacagacaca agcagaaaat tattgcaccg gtg                                2373


<210> SEQ ID NO 5
<211> LENGTH: 40
<212> TYPE: DNA
<213> ORGANISM: Artificial Sequence
<220> FEATURE:
<223> OTHER INFORMATION: AP1-F

<400> SEQUENCE: 5

ttttccttaa gggacaggaa catgctgtgt ttgcctgcgt                           40


<210> SEQ ID NO 6
<211> LENGTH: 39
<212> TYPE: DNA
<213> ORGANISM: Artificial Sequence
<220> FEATURE:
<223> OTHER INFORMATION: AP1-R

<400> SEQUENCE: 6

tattttcacc ggtgcaataa ttttctgctt gtgtctgtc                            39


<210> SEQ ID NO 7
<211> LENGTH: 18
<212> TYPE: DNA
<213> ORGANISM: Artificial Sequence
<220> FEATURE:
<223> OTHER INFORMATION: Primer oligNot I

<400> SEQUENCE: 7

ttttctagag cggccgct                                                   18
```

RECOMBINANT BIVALENT INACTIVATED VACCINE AGAINST FOOT-AND-MOUTH DISEASE VIRUS, PREPARATION METHOD AND USE THEREOF

INCORPORATION BY REFERENCE

The instant application contains a Sequence Listing which has been submitted in ASCII format via EFS-Web and is hereby incorporated by reference in its entirety. Said ASCII copy was amended on Aug. 6, 2020, is named 104146_0001US_SEQLISTING_AMENDED.txt, and is 9,205 bytes in size.

TECHNICAL FIELD

The present disclosure belongs to the field of biotechnology and biological preparations, in particular, relates to a vaccine composition against type O and non-O type (e.g., type A) foot-and-mouth disease virus, a preparation method and uses thereof.

BACKGROUND ART

Foot-and-mouth disease (FMD) is an acute, febrile, highly contagious disease of cloven-hoofed animals such as swine, cattle, and sheep caused by the foot-and-mouth disease virus (FMDV). FMDV includes seven serotypes: A, O, Asia1, C, SAT1, SAT2, and SAT3 with no cross-protection between different serotypes.

Over the years, the two serotypes of FMDV, type O and type A FMDV, have caused serious damage and economic losses to the breeding industry in China. After changing the vaccine strains of type Asia1 FMDV in 2007, the outbreak of type Asia1 FMD was quickly and effectively controlled. There were no clinical reports after 2009 and the type Asia1 FMD tends to be extinct. In 2010, type O Mya-98 strains were introduced into China, causing serious outbreaks, making the type O FMD that was endemic in China more complicated; type A SEA-97 G1 strains and G2 strains were introduced into China in 2009 and 2013 respectively, causing outbreaks in many provinces and enormous losses.

At present, the two serotypes of FMDV, type O and type A FMDV, are mainly prevalent in China. The predominant strains are type O Mya-98 lineage strains, PanAsia lineage strains and type A SEA-97 G2 lineage strains. Due to the complex status of domestic and neighboring epidemics of FMD and absence of cross-immune reaction and cross-protection between different serotypes, it is urgent to develop specific vaccines against the type O and type A epidemic strains that reveal high protective efficiency and broad spectrum. The developed vaccines must be able to prevent multiple strains at the same time and provide efficient protection against the epidemic strains. The expected vaccines will be effective tools for FMD control in China and the neighboring countries.

The reverse genetic techniques can be used for modification and reconstruction of viral genes that overcome the natural constraints of vaccine development such as being time-consuming and laborious, poor antigenicity, and late antibody response for domesticating vaccine strains from epidemic strains. The reverse genetic techniques-mediated construction and modification of vaccine strains make the vaccine development more motivated and convenient. Therefore, this study uses the established reverse genetics operating system with strong cell immune response strains as a framework to prepare a vaccine strain containing the selected type O Mya-98 strain antigen framework, then develops bivalent inactivated vaccines against both serotype O and A FMDV by combining the recombinant serotype O FMD vaccine strains with the recombinant type A FMD vaccine strains that have been developed successfully by means of reverse genetics techniques. The bivalent vaccines prepared are characterized by good production performance, good antigen matching, wide antigen spectrum, and can simultaneously prevent the outbreak of type O and type A FMD showing strong immune efficacy and long duration of immune efficiency.

SUMMARY OF THE DISCLOSURE

The disclosure relates to a foot-and-mouth disease virus (FMDV) vaccine composition, a method for preparing the FMDV vaccine composition, and the use of the FMDV vaccine composition in developing medicines for preventing and/or controlling foot-and-mouth disease in animals.

In one aspect, the present disclosure relates to an FMDV vaccine composition.

In certain embodiments, the FMDV vaccine composition comprises a first FMDV vaccine and a second FMDV vaccine, the first FMDV vaccine comprising a first foot-and-mouth disease virus containing first recombinant FMDV nucleic acids or the same encoded by the first recombinant FMDV nucleic acids. The sequence of the first recombinant FMDV nucleic acids comprises a nucleic acid sequence of an FMDV non-O/JSCZ/2013 strain, but the adjacent L gene, P1 gene, and P2 gene in the nucleic acid sequence of the FMDV non-O/JSCZ/2013 strain are replaced as a whole by a corresponding gene fragment in the nucleic acid sequence of the O/JSCZ/2013 strain, the second. FMDV vaccine is a non-O type FMDV strain.

In the present application, the term "non-O type FMDV strain" refers to a FMDV strain of which a part or all of its nucleic acids are not derived from a serotype O FMDV strain, but, for example, derived from a type A, Asia1, C, SAT1, SAT2 or SAT3S FMDV strain.

In certain embodiments, the corresponding gene fragment in the nucleic acid sequence of the O/JSCZ/2013 strain is equal or not equal in length to the adjacent L gene, P1 gene, and P2 gene in the nucleic acid sequence of the FMDV non-O/JSCZ/2013 strain. In certain embodiments, the corresponding gene fragment in the nucleic acid sequence of the O/JSCZ/2013 strain is shown in SEQ ID NO: 1. In certain embodiments, the sequence of the L gene that is to be replaced in the FMDV non-O/JSCZ/2013 strain is a sequence of at least 100 consecutive nucleotides connected with P1 gene, in the L gene of the FMDV non-O/JSCZ/2013 strain, e.g. a sequence of 105, 110, 115, 120, 125, 130, 135, 140, 145, 150, 155, 160, 165, 170, 171, 172, 173, 174, 175, 176, 177, 178, 179, or 180 consecutive nucleotides. In certain embodiments, the sequence of the L gene that is to be replaced in the FMDV non-O/JSCZ/2013 strain is a sequence of 177 consecutive nucleotides connected with P1 gene, in the L gene of the FMDV non-O/JSCZ/2013 strain. In certain embodiments, the sequence of the P2 gene to be replaced in the FMDV non-O/JSCZ/2013 strain is a sequence of at least 1000 consecutive nucleotides connected with P1 gene, in the P2 gene of the FMDV non-O/JSCZ/2013 strain, e.g. a sequence of 1050, 1100, 1150, 1200, 1201, 1202, 1203, 1204, 1205, 1206, 1207, 1208, 1209 or 1210 consecutive nucleotides. In certain embodiments, the sequence of the P2 gene that is to be replaced in the FMDV non-O/JSCZ/2013 strain is a sequence of 1206 consecutive nucleotides connected with P1 gene, in the P2 gene of the FMDV non-O/JSCZ/2013 strain. In certain embodiments, 177 consecutive nucleotides in the L gene connected with P1 gene, all of the P1 gene and 1206 consecutive nucleotides in P2 gene connected with the P1 gene, in the FMDV non-O/JSCZ/2013 strain, are replaced as a whole by the sequence shown in SECS ID NO: 1.

As known to those skilled in the art, in the genome of the FMDV, the L gene, the P1 gene and the P2 gene are arranged in sequence from the 5' end to the 3° end. In the present application, "the adjacent L gene, P1 gene, and P2 gene" refers to that the 3' end of the L gene is operably linked to the 5' end of the P1 gene, and the 3' end of the P1 gene is operably linked to the 5' end of the P2 gene.

In the present application, the term "L gene" refers to a part or all of the L gene in the genome of the FMDV, for example, a sequence of at least 100 consecutive nucleotides connected with P1 gene, in the L gene of the FMDV non-O/JSCZ/2013 strain, e.g. a sequence of 105, 110, 115, 120, 125, 130, 135, 140, 145, 150, 155, 160, 165, 170, 171, 172, 173, 174, 175, 176, 177, 178, 179, or 180 consecutive nucleotides.

In the present application, the term "P2 gene" refers to a part or all of the P2 gene in the genome of the FMDV, for example, a sequence of at least 1000 consecutive nucleotides connected with P1 gene, in the P2 gene of the FMDV non-O/JSCZ/2013 strain, e.g. a sequence of 1050, 1100, 1150, 1200, 1201, 1202, 1203, 1204, 1205, 1206, 1207, 1208, 1209, or 1210 consecutive nucleotides.

In the present application, "a corresponding gene fragment in the nucleic acid sequence of the O/JSCZ/2013 strain" refers to the adjacent L gene, P1 gene, and P2 gene in the genome of the FMDV O/JSCZ/2013 strain, wherein the L gene can be a part or all of the L gene of the O/JSCZ/2013 strain, and the P2 gene can be a part or all of the P2 gene of the O/JSCZ/2013 strain.

In the present application, "FMDV non-O/JSCZ/2013 strain" means that an FMDV strain of which a part or all of the nucleic acids are not derived from O/JSCZ/2013 strain, but, for example, derived from FMDV O/CHA/99 strain, O/GDBY/2010 strain, A/OD/2013 strain or a highly efficient vaccine strains recommended by OIE (World Organisation for Animal Health). In certain embodiments, the FMDV non-O/JSCZ/2013 strain is O/CHA/99 strain.

In certain embodiments, the first EMDV vaccine is a type O FMDV vaccine strain. In certain embodiments, the first FMDV vaccine is capable of stimulating immune activity against the type O FMDV strain.

In certain embodiments, the type O FMDV strain is a Mya-98, PanAsia or Cathay lineage strain. In certain embodiments, the type O FMDV strain is O/BY/CHA/2010, O/0834 or O/0718 strain, and the $PD_{50}$ value of the first FMDV vaccine against O/BY/CHA/2010, O/0834 or O/0718 strain in each case is greater than 6.

In certain embodiments, the second FMDV vaccine comprises an FMDV vaccine strain of any of the serotypes A, Asia1, C, SAT1, SAT2, and SAT3. In certain embodiments, the second FMDV vaccine is a type A FMDV vaccine strain. In certain embodiments, the second FMDV vaccine is capable of stimulating immune activity against the type A FMDV strain. In certain embodiments, the type A FMDV vaccine is SEA-97G1 or SEA-97G2 strain. In certain embodiments, the type A FMDV strain is A/WH/CHA/09 or A/GDMM/2013 strain, and the $PD_{50}$ value of the second FMDV vaccine against A/WH/CHA/09 or A/GDMM/2013 strain in each case is greater than 6. In certain embodiments, the second FMDV vaccine is a recombinant type A FMDV vaccine strain. In certain embodiments, the recombinant type A FMDV vaccine strain comprises a nucleic acid sequence shown in SEQ ID NO: 4.

In certain embodiments, the genome of the recombinant type A FMDV vaccine strain comprises the nucleic acid sequence of the FMDV O/CHA/99 strain, but a part of the L gene and the adjacent P1 gene are replaced as a whole by a corresponding gene fragment in the nucleic acid sequence of the FMDV A/WH/CHA/09 strain. In certain embodiments, the corresponding gene fragment in the nucleic acid sequence of the A/WH/CHA/09 strain is equal or not equal in length to the part of the L gene and the P1 gene of the O/CHA/99 strain. In certain embodiments, the corresponding gene fragment in the nucleic acid sequence of the A/WH/CHA/09 strain is shown in SEQ ID NO: 4.

In the present application, "a part of the L gene and the adjacent P1 gene" means that the 3' end of a part of the L gene is operably linked to the 5' end of the P1 gene.

In the present application, "a corresponding gene fragment in the nucleic acid sequence of the FMDV A/WH/CHA/09 strain" refers to the adjacent L gene and P1 gene in the genome of the FMDV A/WH/CHA/09 strain, wherein the L gene can be a part or all of the L gene of the A/WH/CHA/09 strain, and the P1 gene can be a part or all of the P1 gene of the A/WH/CHA/09 strain.

In certain embodiments, there is no immunosuppression between the first FMDV vaccine and the second FMDV vaccine. In the present application, "no immunosuppression" means that the first FMDV vaccine and the second FMDV vaccine do not significantly weaken each other's immune effects after immunizing an animal.

In certain embodiments, the FMDV vaccine composition is capable of stimulating immune activity against the type O FMDV strain. In certain embodiments, the type O FMDV strain is an epidemic strain of Mya-98, PanAsia or Cathay lineage. In certain embodiments, the type O FMDV strain is O/BY/CHA/2010, O/0834 or O/0718 strain, and the $PD_{50}$ value of the vaccine composition against O/BY/CHA/2010, O/0834 or O/0718 strain in each case is greater than 6. The O/BY/CHA/2010 strain was deposited with the accession number of FMDV10033 at the OIE/China National Foot and Mouth Disease Reference Laboratory designated by Veterinary Bureau of Ministry of Agriculture and Rural Affairs of the People's Republic of China (abbreviated as CNFMDRL), having an address of NO.1 Xujiaping, Chengguan District, Lanzhou City, Gansu province, P.R. China, on Mar. 1, 2017. The O/0834 strain was deposited with the accession number of FMDV08034 at the CNFMDRL on Mar. 1, 2017. The O/0718 strain was deposited with the accession number of FMDV07018 at the CNFMDRL on Mar. 1, 2017.

In certain embodiments, the FMDV vaccine composition is capable of stimulating immune activity against the type A FMDV strain. In certain embodiments, the type A FMDV vaccine is SEA-97G1 or SEA-97G2 strain. In certain embodiments, the type A FMDV strain is A/WH/CHA/09 or A/GDMM/2013 strain, and the $PD_{50}$ value of the vaccine composition against A/WH/CHA/09 or A/GDMM/2013 strain in each case is greater than 6.

In another aspect, the present disclosure relates to a method for preparing an FMDV vaccine composition, comprising the following steps: (a) cultivating a first FMDV vaccine strain and collecting the first FMDV vaccine strain; (b) cultivating a second FMDV vaccine strain and collecting the second FMDV vaccine strain; c) inactivating the first FMDV vaccine strain collected in step (a) and the second FMDV vaccine strain collected in step (b) and then mixing both. In certain embodiments, the FMDV vaccine strains are emulsified after mixing. In certain embodiments, the emulsification is performed with ISA 206 adjuvant in a volume ratio of 1:1.

In some embodiments, the step (a) comprises the following steps:

1) mixing the specific primers OP12A-F and OP12A-R with cDNA of O/JSCZ/2013 strain to obtain a gene fragment of L, P1 and P2 genes of O/JSCZ/2013 strain through amplification, and inserting the obtained gene fragment into the eukaryotic transcription plasmid prO/CHA/99 by replacement to obtain a recombinant plasmid prO-FMDV, the specific primers are respectively

```
OP12A-F:
                                          (SEQ ID NO: 2)
5'-TTTTCCTTAAGGGACAGGAACACGCCGTGTTTGCCTGCGT-3',

OP12A-R:
                                          (SEQ ID NO: 3)
5'-ACTCACATCGATGTCAAAGTGAAACCTTC-3';
```

2) transfecting FMDV-sensitive cells with the recombinant plasmid prO-FMDV obtained in step 1) to obtain a first FMDV vaccine strain.

In certain embodiments, the L gene, P1 gene and P2 gene of O/JSCZ/2013 strain comprise the nucleic acid sequence shown in SEQ ID NO:1. In certain embodiments, the FMDV-sensitive cell is BHK-21 cell or IBRS-2 cell. In certain embodiments, the 146S antigen content of the obtained first FMDV vaccine strain is 4.0μ/mL or more (the method for determining the 146S antigen content is described in Chinese patent ZL201310017378.8, the entire contents of which are incorporated by reference). In certain embodiments, the inactivation is performed with binary ethylenimine. In certain embodiments, the first FMDV vaccine strain is emulsified after inactivation. In certain embodiments, the emulsification is performed with ISA 206 adjuvant in a volume ratio of 1:1.

In some embodiments, the step (b) comprises the following steps:

1) mixing the specific primers AP1-F and AP1-R with cDNA of A/WH/CHA/09 strain to obtain a gene fragment of a part of the L gene and P1 gene of A/WH/CHA/09 strain through amplification, and inserting the obtained gene fragment into the eukaryotic transcription plasmid prO/CHA/99 by replacement to obtain a recombinant plasmid prA-FMDV, the specific primers are respectively

```
AP1-F:
                                          (SEQ ID NO: 5)
5'-ttttccttaagggacaggaacatgctgtgtttgcctgcgt-3';

AP1-R:
                                          (SEQ ID NO: 6)
5'-tattttcaccggtgcaataattttctgcttgtgtctgtc-3';
```

2) transfecting FMDV-sensitive cells with the recombinant plasmid prA-FMDV obtained in step 1) to obtain a second FMDV vaccine strain.

In certain embodiments, the second FMDV vaccine strain comprises a nucleic acid sequence shown in SEQ ID NO: 4. In certain embodiments, the FMDV-sensitive cell is BHK-21 cell or IBRS-2 cell. In certain embodiments, the 146S antigen content of the obtained second FMDV vaccine strain is 4.0 μg/mL or more (the method for determining the 146S antigen content is described in Chinese patent ZL201310017209.4, the entire contents of which are incorporated by reference). In certain embodiments, the inactivation is performed with binary ethylenimine. In certain embodiments, the second FMDV vaccine strain is emulsified after inactivation. In certain embodiments, the emulsification is performed with ISA 206 adjuvant in a volume ratio of 1:1.

In certain embodiments, the first FMDV vaccine strain and the second FMDV vaccine strain are adapted to suspension cell culture. In certain embodiments, the first FMDV vaccine strain and the second FMDV vaccine strain can be mixed in an appropriate ratio. The first FMDV vaccine strain and the second. FMDV vaccine strain can be respectively made into an antigen solution with a certain virus titer, and after inactivation, the mixing ratio is calculated based on the measured antigen content. In certain embodiments, the first FMDV vaccine strain and the second FMDV vaccine strain are mixed in an antigen content ratio of 4:1 to 1:4, for example, in an antigen content of 4:1, 3:1, 2:1, 1:1, 1:1.5, 1:2, 1:2.5, 1:3, 1:3.5, or 1:4. In certain embodiments, the mixing is performed by mixing the first FMDV vaccine strain and the second FMDV vaccine strain in a 1:1 ratio of antigen content. In certain embodiments, the inactivation is performed with binary ethylenimine. In certain embodiments, the vaccine composition is emulsified after inactivation. In certain embodiments, the emulsification is performed with ISA 206 adjuvant in a volume ratio of 1:1.

In another aspect, the present disclosure relates to the use of the FMDV vaccine composition in preparing medicines for preventing and/or controlling animal foot-and-mouth disease. In certain embodiments, the foot-and-mouth disease is type A, O, C, Asia1, SAT1, SAT2, or SAT3 foot-and-mouth disease. In certain embodiments, the foot-and-mouth disease is type O foot-and-mouth disease. In certain embodiments, the foot-and-mouth disease is type A foot-and-mouth disease. In certain embodiments, the animal is a cloven-hoofed animal. In certain embodiments, the animal is swine, cattle or sheep.

The present disclosure has the following positive effects:

The present disclosure utilizes a mature reverse genetic technology to construct a recombinant type O vaccine strain with accelerated CPE formation activity, high virus titer, high antigen matching, and high virus yield performance, and prepares a bivalent (type O and type A) inactivated vaccine against FMDV by combining the recombinant type O vaccine strain with the recombinant type A FMD vaccine strains which have been prepared successfully. The bivalent vaccine prepared is characterized by good production performance, good antigen matching, wide antigen spectrum, and can simultaneously prevent the type O and type A foot-and-mouth disease and have strong immunogenicity and long duration of immune efficacy. The present disclosure has solved the problems of the production and domestication of selected vaccine seed virus, and has achieved the first case of preparing a highly effective bivalent inactivated vaccine by using the vaccine strain constructed by reverse genetic technology.

1) The developed bivalent vaccine shows improved production performance at the virus level, the CPE formation time of the recombinant type O vaccine strain and the recombinant type A vaccine strain is considerably reduced, the virus titer is increased, and the antigen production cost is reduced;

2) The antigen matching and immune response of vaccine strains can be improved, the structural proteins of the recombinant type O vaccine strain and the recombinant type A vaccine strain of the present disclosure are identical to those of the epidemic strains, and their antigens are completely matched with those of the epidemic strains, and the specificity and efficacy of the vaccine strain to epidemic strains can be highly improved.

3) The type O FMDV recombinant vaccine strain and the type A FMDV recombinant vaccine strain of the present disclosure can both rapidly and massively proliferate on the BHK-21 suspension cells, and the optimal collection time for the type O recombinant vaccine strain is 8 to 14 hours after virus incubation, and the antigen content can reach up to 4.0 μg/mL or more. The antigen content can reach up to 4.0 μg/mL or more with the collection time at 6 to 10 hours after inoculation of type A recombinant vaccine strain. The increase in antigen content effectively saves production costs.

4) The type O FMDV recombinant vaccine strain and the type A FMDV recombinant vaccine strain of the present disclosure both have a wide spectrum of antigens. The structural protein of the type O recombinant vaccine strain was amplified from the Mya_98 strain selected by large-scale screening. The antigenic sites of the selected strain are well matched to those of the epidemic strains of the present lineage and overlapped with antigens of the epidemic strains of other lineages, PanAsia and Cathay topotype strains. The cross-immunity challenge test showed that the type 0 FMDV recombinant vaccine strain can effectively protect the Mya_98, PanAsia and Cathay epidemic strains; the type A FMDV recombinant vaccine strain can also provide cross-immunity protection, and can effectively protect against the SEA-97G1 strain and G2 strain, and thus a broad spectrum of antigens for the vaccine can be achieved.

5) Prepared type O and type A FMDV bivalent inactivated vaccines can effectively stimulate the body of animals to produce immune responses after immunizing the animals. Type O antigens and type A antigens can synergistically enhance immune responses. The duration of immune efficacy is increased to about 6 months, and the immunogenicity of the FMDV vaccine is greatly enhanced.

6) The technology of the disclosure overcomes defects of screening and domestication of field virus strain such as significant constraint by the nature property of the virus, time- and labor-consuming and low success rate, realizes more active and effective construction of vaccine strains, and further realizes the innovation of preparation techniques of virus seeds for inactivated FMDV vaccines, and has significant application value.

DETAILED DESCRIPTION OF THE PREFERRED EMBODIMENT(S)

The disclosure combines accumulation of strains in the National Foot-and-Mouth Disease Reference Laboratory in recent years and analysis of the whole genome sequences of the strains, and amplifies the L gene, P1 gene and P2 gene from the type O FMDV O/JSCZ/2013 strain. Through choosing appropriate restriction endonuclease sites, corresponding nucleotide sequence in the established rescue system of type O FMDV O/CHA/99 strain is replaced with the L-P1-P2 gene of the type O FMDV O/JSCZ/2013 strain, so as to obtain a recombinant type O FMDV plasmid prO-FMDV; once plasmid is rescued on BHK-21 cells or IBRS-2 cells, a recombinant type O FMDV rO-FMDV is obtained, which was completely matched with the antigen of epidemic strains, and overlapped with antigens of epidemic strains of PanAsia and Cathay lineage, with wide spectrum of antigens. The recombinant vaccine strain produced by suspended BHK-21 cells has good production performance, and its antigen content can reach 4.0 μg/mL or more. The prepared vaccine can effectively stimulate the body to produce strong antibody response, and is characterized with high titers, high antigen producing capacity, wide spectrum of antigens, reduced pathogenicity, higher level of antibody response, and high immune protection efficacy. The recombinant type O FMDV vaccine strain is combined with a successfully developed recombinant type A FMDV vaccine strain, which is constructed by using reverse genetic technology, to prepare the type O and type A bivalent inactivated vaccines for foot-and-mouth disease. After immunization of swine and cattle, the bivalent vaccine is effective in stimulating the production of strong immune response of body, with high level of antibody response, synergistic enhancement of immune response between antigens, high immune protection efficacy, and long duration of immune efficacy. For the type O Mya_98 strain, PanAsia strain, Cathay train, type A SEA-97G1 strain and G2 strain that are currently prevalent in China, the vaccine can provide good immune protection efficacy to these strains.

The present disclosure will be further described with reference to specific embodiments, but the specific implementation does not limit the present disclosure.

Unless particularly stated, the experimental methods used in the following examples are all under conventional conditions, such as the methods described in "Short protocols in molecular biology" edited by Ausubel, F. M., Kingston, R E., Seidman, J. G., et al. and translated by MA, X. and Shu, Y. Beijing: Science Press, 2004).

Example 1. Construction of Infectious Clones of Recombinant Type O FMDV

Figure 1:
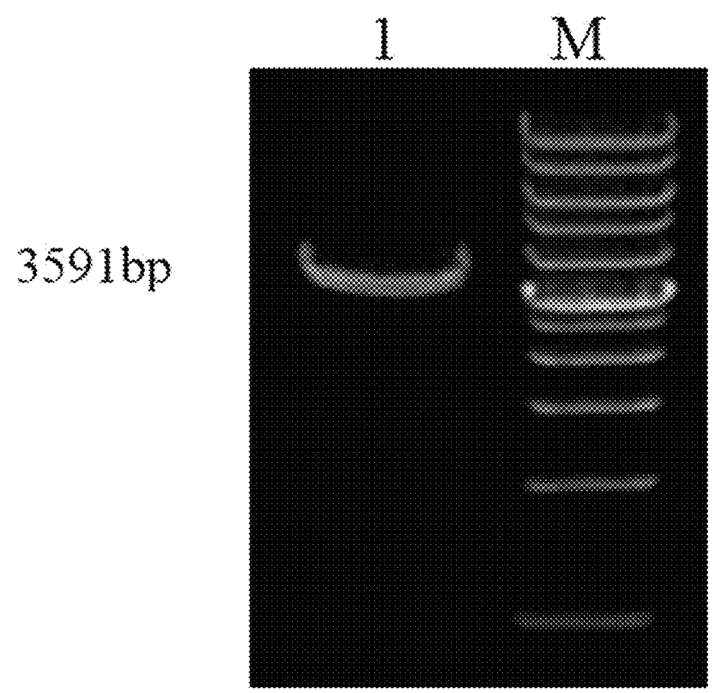
FIG. 1 is an electrophoretogram of the gene fragment of L, P1 gene and P2 gene of FMDV O/JSCZ/2013 strain in Example 1, in which 1 is an amplified fragment and M is a DNA marker.

The O/JSCZ/2013 strain used by 5' the inventor was deposited at the OIE/China National Foot and Mouth Disease Reference Laboratory designated by Veterinary Bureau of Ministry of Agriculture and Rural Affairs of the People's Republic of China (abbreviated as CNFMDRL), of which the address is NO.1 Xujiaping, Chengguan District, Lanzhou, Gansu Province, China. The O/JSCZ/2013 strain was deposited on Mar. 1, 2017 with the accession number of FMDV13084, which can be obtained by the public with a letter of authorization issued by Veterinary Bureau of Ministry of Agriculture and Rural Affairs of the People's Republic of China. The O/CHA/99 strain was deposited with the accession number of FMDV1999001 at the CNFMDRL on Jun. 1, 2012. Based on the genome sequence of the O/JSCZ/2013 strain, a pair of amplification primers OP12A-F (5'-TTTTCCTTAAGGGACAGGAACACGCCGTGTTTGCCTGCGT-3', SEQ ID NO:2) and OP12A-R (5'-ACTCACATCGATGTCAAAGTGAAACCTTC-3', SEQ ID NO:3) were designed and synthesized. Total RNA of the O/JSCZ/2013 strain was extracted using the RNeasy Mini Kit (Qiagen), and reverse transcribed by the primer oligNot I (5'-ttttctagagcggccgct$_{38}$-3', SEQ ID NO:7) to synthesize the first-strand complementary DNA (cDNA). PrimeScript Reverse Transcriptase (TaKaRa) with extremely high extension capability was used. A 20 μL of reaction system was prepared according to the manufacture's instruction and reacted at 42° C. for 1 h for further use. By using the reverse-transcribed first-strand cDNA as a template and mixing the primers OP12A-F and OP12A-R with the cDNA nucleic acids of the O/JSCZ/2013 strain, gene fragments of the O/JSCZ/2013 strain were amplified. The amplification was performed with LATaq® DNA polymerase (TaKaRa), which is suitable for long fragment amplification with excellent performance. A 50 μL of reaction system was prepared according to the manufacture's instruction, of which the amplification conditions were as follows: 94° C. for 5 min; 35 cycles of 94° C. for 30 s, 57° C. for 30 s and 72° C. for 3.5 min; followed by 72° C. for 10 min. PCR amplified products were purified and recovered and sent for nucleotides sequencing. The electrophoresis results of the amplified products were shown in FIG. 1, with a size of 3591 bp, consistent with the expected size. The sequencing result shows the nucleotide sequence of the amplified product is as shown in the sequence of SEQ ID NO: 1.

Figure 2:
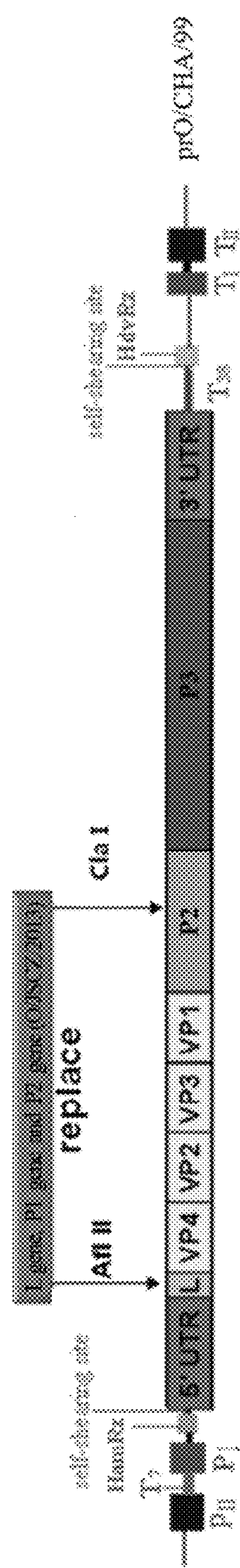
FIG. 2 is a schematic diagram of the construction strategy of the recombinant plasmid prO-FMDV of type O foot-and mouth disease virus (FMDV) in Example 1.

The obtained plasmid prO/CHA/99 containing a gene fragment of L, P1 and P2 genes of the O/JSCZ/2013 strain and the rescue system of type O foot-and-mouth disease virus O/CHA/99 strain (disclosed in a granted patent "recombinant type Asia1 FMDV and preparation method and use thereof" ZL201310175323.X and "recombinant type A FMDV vaccine strain and preparation method and use thereof" ZL201310175324.4, the full texts of which are both incorporated into this application by reference) was digested with AflII and ClaI, respectively, the corresponding target fragment was purified and recovered, ligated and transformed into JM109 competent cells. The positive clones were identified by sequencing, and the recombinant plasmid prO-FMDV containing L gene, P1 and P2 genes of the O/JSCZ/2013 strain was obtained. The construction method is shown in FIG. 2.

Example 2. Rescue of Recombinant Type O FMDV

Figure 3:
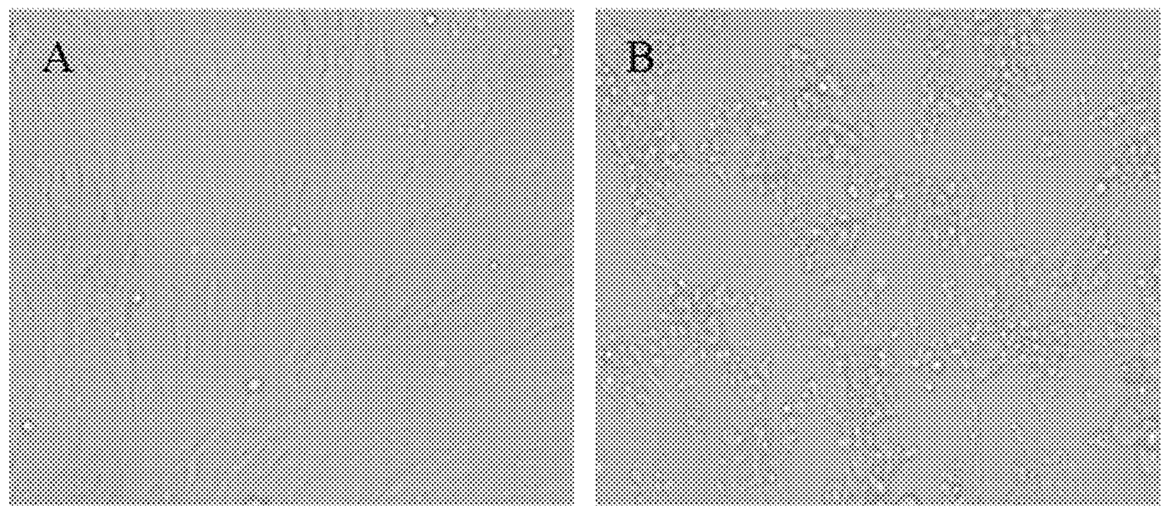
FIG. 3 is the cytopathic effect (CPE) caused by the recombinant virus rO-FMDV in BHK-21 cells in Example 2, in which A denotes normal BHK-21 cells; B denotes BHK-21 cells with CPE.

The recombinant plasmid prO-FMDV obtained in Example 1 was prepared by using a QIAGEN® Plasmid Plus Maxi Kit (QIAGEN). BHK-21 cells were used for transfection when they were grown to 80%. 4 μg of the recombinant plasmid was transfected into BHK-21 cells using liposome Lipofectamine™2000 (Invitrogen), meanwhile liposome control and normal cell control were set up, the cells were cultured at 37° C. in an incubator containing 5% $CO_2$. After 6 hours of transfection, the supernatant was discarded and the MEM medium was added. Cultivation was continued, and cell state and cell pathological changes were observed. The virus was harvested until the cytopathic effect (CPE) reached to about 90%. Freezing and thawing was repeated three times and then BHK-21 cells were inoculated again until the virus can stably produce CPE, i.e., the infected cells became round and were accumulated into grape-like distribution, eventually disintegrated into debris. The obtained recombinant type O FMDV was named as rO-FMDV. In FIG. 3, panel A is a picture of normal control BHK-21 cells; panel B is a picture of the CPE appearing in the BHK-21 cells infected with the rescued recombinant virus rO-FMDV.

Example 3. Identification of Recombinant Type O FMDV by PCR

Total RNA was extracted from the supernatant of BHK-21 cells infected with the stably passaged recombinant virus rO-FMDV by the RNeasy Mini Kit (Qiagen), and then reverse-transcribed, amplified, purified, recovered, and sent for nucleotide sequencing. The result shows that the gene sequence containing the L, P1 and P2 genes of the recombinant type O FMDV is identical to that of the O/JSCZ/2013 strain.

Example 4. Construction of Infectious Clones of Recombinant Type A FMDV

The A/WH/CHA/09 strain used by the inventor was deposited at the OIE/China National Foot and Mouth Disease Reference Laboratory designated by Veterinary Bureau of Ministry of Agriculture and Rural Affairs of the People's Republic of China, having an address of NO.1 Xujiaping, Chengguan District, Lanzhou, Gansu Province, China, on Jun. 1, 2012 with the accession number of FMDV09012, which can be obtained by the public with a letter of authorization issued by Veterinary Bureau of Ministry of Agriculture and Rural Affairs of the People's Republic of China. Total RNA of the A/WH/CHA/09 strain was extracted using the RNeasy Mini Kit (Qiagen), and reverse transcribed by the primer oligNot I (5'-ttttctagagcggccgct$_{38}$-3', SEQ ID NO:7) to synthesize the first-strand cDNA. By using the synthesized first-strand cDNA as a template and amplifying with the primers AP1-F(5'-ttttccttaagggacaggaacatgctgtgtttgcctgcgt-3', SEQ ID NO:5) and AP1-R(5'-tattttcaccggtgcaataattttctgcttgtgtctgtc-3', SEQ ID NO: 6), a gene fragment of the A/WH/CHA/09 strain was obtained. The amplification was performed with LATaq® DNA polymerase (TaKaRa), which is suitable for long fragment amplification and with excellent performance, a 50 μL of reaction system was prepared according to the manufacture's instruction, of which the amplification conditions were as follows: 94° C. for 5 min; 35 cycles of 94° C. min for 30 s, 57° C. for 30 s, and 72° C. for 2.5 min; followed by 72° C. for 8 min. PCR amplified products were confirmed by 0.8% agarose gel electrophoresis, and then purified and recovered and sent for nucleotide sequencing. The sequencing result shows that the nucleotide sequence of the amplified product is same as the sequence of SEQ ID NO: 4.

The obtained plasmid prO/CHA/99 containing a gene fragment of a part of L gene with the P1 gene of the A/WH/CHA/09 strain and the rescue system of type O FMDV O/CHA/99 strain was digested with AflII and SgrAI, respectively, the corresponding target fragments were purified and recovered, ligated and transformed into JM109 competent cells. The positive clones were identified by nucleotide sequencing, and the recombinant plasmid prA-FMDV containing a part of leader protein L and structural protein P1 of the A/WH/CHA/09 strain was obtained (the used plasmid and methods are disclosed in a granted patent "recombinant type A FMDV and preparation method and use thereof" ZL201310175324.4, the full texts of which are both incorporated into this application by reference).

Example 5. Rescue of Recombinant Type A FMDV

The recombinant plasmid prA-FMDV obtained in Example 4 was prepared by a QIAGEN® Plasmid Plus Maxi Kit (QIAGEN). BHK-21 cells were used for transfection when they were grown to 80%. 4 μg of the recombinant plasmid was transfected into BHK-21 cells by liposome Lipofectamine™2000 (Invitrogen), meanwhile liposome control and normal cell control were set up, and the cells were placed at 37° C. in an incubator containing 5% $CO_2$. After 6 hours of transfection, the supernatant was discarded and MEM medium was added. Cultivation was continued, and the cell state and cell pathological changes were observed. The virus was harvested until the cytopathic effect (CPE) reached to about 90%. Freezing and thawing was repeated three times and then the collected virus was used to inoculate BHK-21 cells again until stable CPE appeared, i.e., the infected cells became round and were accumulated into grape-like distribution, eventually disintegrated into debris. The obtained recombinant type A FMDV was named as rA-FMDV.

Example 6. Identification of Recombinant Type A FMDV by RT-PCR

Total RNA was extracted from the supernatant of BHK-21 cells infected with the stably passaged recombinant virus rO-rA-FMDV using the RNeasy Mini Kit (Qiagen), and then reverse-transcribed, amplified, purified, recovered, and sent for nucleotide sequencing. The result shows that the gene sequence including a part of L gene and P1 gene of the recombinant type A FMDV is identical to that of the A/WH/CHA/09 strain.

Example 7. Pathogenicity Test of Recombinant Type A and Type O FMDV Vaccine Strains on BHK-21 Cells 7.1 Pathogenicity Test of Recombinant type O FMDV Vaccine Strain on BHK-21 Cells BHK-21 cells were passaged and cultured according to the conventional method, and MEM cell culture medium containing 10% fetal bovine serum was used to maintain the cultures; the suspended cells was dispersed in a 12-well plate, and cultured in an incubator containing 5% $CO_2$ at 37° C. until a monolayer of cells reached 90%. The virus solution was diluted 10-fold with MEM, and each dilution ($10^{-4.0}$-$10^{-9.0}$) of the virus solution was added to the cell plate (4 wells for each dilution), and cultured in an incubator containing 5% $CO_2$ at 37° C. The cells were cultured and observed for 3 days, and the median tissue culture infectious dose ($TCID_{50}$) on BHK-21 cells was measured by the Reed-Muench's method. According to this method, the titers of rO-FMDV were determined, and the $TCID_{50}$ of the type O FMDV vaccine strain rO-FMDV was calculated to be $10^{-8.33}$/mL.

The Reed-Muench method is a previously established method in the field, and the method has been described in detail in the published reference "Reed, L J and Muench, H. (1938). "A Simple Method of Estimating Fifty Percent Endpoints". The American. Journal of Hygiene 27:493-497", which is hereby incorporated as a reference into this application.

7.1 Pathogenicity Test of Recombinant Type A FMDV Vaccine Strain on BHK-21 Cells In accordance with the method described in 7.1, the median tissue culture infectious dose ($TCID_{50}$) of recombinant type A FMDV vaccine strain rA-FMDV on BHK-21 cells was determined. The $TCID_{50}$ of the type A FMDV vaccine strain rO-FMDV was calculated to be $10^{-833}$/mL.

Example 8. Culture of Recombinant Type A and Type O FMDV Vaccine Strains on BHK-21 Suspension Cells 8.1 Sensitivity Test of BHK-21 Suspension Cells on Recombinant Type O FMDV Vaccine Strain Suspension cells in a 5 L bioreactor were inoculated with the recombinant type O FMDV vaccine strain rO-FMDV which had been cultured and harvested using adherent BHK-21 cells, then suitable conditions such as dissolved oxygen, temperature, pH and rotation speed were set. The cell morphology and the virus content of the sample (Table 1) were observed and measured with a fixed sampling time interval. The result shows that the vaccine strain can be well adapted to BHK-21 suspension cells with quick CPE appearance and high antigen content which can reach 4.0 μg/ml or more, which meets the requirement for preparing vaccines. After serial passage of the suspension cells for five generations, RT-PCR amplification and nucleotide sequencing was performed to observe nucleotide mutation via sequences alignment. The result indicates that the strain shows good stability, and the type O FMDV antigen in the recombinant type O and type A FMDV bivalent inactivated vaccine can be prepared using the BHK-21 suspension cells.

TABLE 1

Results of suspension adaptation of rO-FMDV vaccine strain

| rO-FMDV | | Generation: BF15XF1 | | |
|---|---|---|---|---|
| Sample | 2 hours | 6 hours | 10 hours | 12 hours |
| cell viability | 55% | 15% | 2.0% | 0% |
| 146S(μg/ml) | 1.93 | 2.43 | 3.65 | 4.08 |
| rO-FMDV | | Generation: BF15XF2 | | |
| Sample | 2 hours | 6 hours | 10 hours | 12 hours |
| cell viability | 40% | 5.5% | 2% | 0% |
| 146S(μg/ml) | 3.15 | 3.42 | 3.92 | 4.05 |
| rO-FMDV | | Generation: BF15XF3: | | |
| Sample | 2 hours | 6 hours | 10 hours | 14 hours |
| cell viability | 25% | 4.5% | 2% | 0% |
| 146S(μg/ml | 2.08 | 3.50 | 4.18 | 4.20 |
| rO-FMDV | | Generation: BF15XF4: | | |
| Sample | 2 hours | 6 hours | 10 hours | 14 hours |
| cell viability | 30% | 3.5% | 1% | 0% |
| 146S(μg/ml) | 2.22 | 2.26 | 3.75 | 4.58 |
| rO-FMDV | | Generation: BF15XF5 | | |
| Sample | 2 hours | 6 hours | 10 hours | 14 hours |
| cell viability | 35% | 8.5% | 4% | 0% |
| 146S (μg/ml) | 2.98 | 3.72 | 4.01 | 4.23 |
| RT-PCR | — | Homology of 99.8% | — | — |

BHK21 suspension cells have good sensitivity to infection and proliferation of type O FMDV vaccine strain, and it could well achieve replication and proliferation of FMDV in the cells, and show characteristic CPE such as cell death and lysis. The peak of the virus content occurs regularly in a period of 8 to 14 hours, and the antigen 146S was considerably increased. The serial passage showed that the vaccine strain could stably propagated, and the suspension BHK-21 cells can be used to prepare the type 0 FMDV antigen of the recombinant bivalent inactivated vaccine.

8.2 Sensitivity Test of BHK-21 Suspension Cells on Type A Recombinant Vaccine Strain Suspension cells in a 5 L bioreactor were inoculated with the recombinant type A FMDV vaccine strain rO-FMDV which had been cultured and harvested using adherent BHK-21 cells, then suitable conditions such as dissolved oxygen, temperature, pH and rotation speed were set. The cell morphology and the virus content of the sample (Table 2) were observed and measured with a fixed sampling time interval. The result shows that the vaccine strain can be well adapted to BHK-21 suspension cells with quick appearance of CPE and high antigen content which can reach 4.0 or more, which meets the requirement for preparing vaccines. After serial passage of the suspension cells for five generations, RT-PCR amplification and nucleotide sequencing was performed to observe nucleotide mutation via sequences alignment. The result indicates that the strain shows good stability, and the type A FMDV antigen in the recombinant type O and type A FMDV bivalent inactivated vaccine can be prepared using the BHK-21 suspension cells.

TABLE 2

Results of suspension adaptation of rO-FMDV vaccine strain

| rA-FMDV | | Generation of seed virus: BF14XF1 | | |
|---|---|---|---|---|
| Sample | 2 hr: | 6 hr: | 10 hr: | 14 hr: |
| cell viability | 20% | 2% | 0% | — |
| 1.46S(μg/ml) | 2.36 | 3.0 | 4.23 | — |
| rA-FMDV | | Generation of seed virus: BF14XF2 | | |
| Sample | 2 hr: | 6 hr: | 10 hr: | 14 hr: |
| cell viability | 25.5% | 2.5% | 1% | — |
| 146S(μg/ml) | 3.14 | 3.90 | 4.80 | — |
| rA-FMDV | | Generation of seed virus: BF14XF3: | | |
| Sample | 2 hr: | 6 hr: | 10 hr: | 14 hr: |
| cell viability | 35% | 25% | 0% | 0% |
| 146S(μg/ml) | 1.44 | 3.35 | 6.05 | 6.33 |
| rA-FMDV | | Generation of seed virus: BF14XF4: | | |
| Sample | 8 hr: | 10 hr: | 12 hr: | 14 hr: |
| cell viability | 25.5% | 8% | 0% | |
| 146S(μg/ml) | 1.58 | 3.26 | 4.12 | |
| rA-FMDV | | Generation of seed virus: BF14XF5 | | |
| Sample | 8 hr: | 10 hr: | 12 hr: | 14 hr: |
| cell viability | 20% | 4.5% | 0% | 0% |
| 146S(μg/ml) | 5.0 | 4.72 | 4.88 | — |
| RT-PCR | — | Homology of 99.8% | — | — |

After the BHK-21 suspension cells were inoculated with type A recombinant FMDV vaccine strain rA-FMDV, the amount of dissolved oxygen was close to zero in about 7 hours on average. Afterwards, the CPE occurred gradually, and the cells were lysed, and a large number of infectious virus particles were produced, indicating that the virus had a rapid proliferation rate and the time for causing the CPE is shorter than that of other strains. It took 6 to 10 hours for the cells to be substantially destructed, dead and collapsed after inoculating the virus, and cell viability was zero. The content of 146S of virus particles was up to 4.0 μg/mL or more, and even up to 6.33 μg/mL at the time of final virus collection, indicating that the recombinant type A FMDV vaccine strain rA-FMDV can be propagated in a large amount in BHK-21 suspension cells, and the BHK-21 cell line has good sensitivity to the recombinant vaccine strain. Through serial passage of suspension culture for 5 generations, the virus titers and the content of 146S are very high. Sequencing for serial passages proved that the vaccine strain can stably proliferate, and it is totally acceptable to use the BHK-21 suspension cells to produce type A FMDV antigen so as to prepare a recombinant bivalent inactivated vaccine.

Example 9. Preparation of Recombinant Type O FMDV Vaccine and Evaluation of Immune Effect Thereof 9.1 Vaccine Preparation The recombinant virus rO-FMDV prepared by BHK-21 suspension cells was inactivated with 3 mmol/l binary ethylenimine (BEI, Sigma) for 30 h at 30° C., and a blocker sodium thiosulfate solution was added. The mixture was stored overnight at 4° C. for further use. After a safety test, the inactivated antigen was prepared and mixed with ISA 206 adjuvant (SEPPIC, France) in a 1:1 ratio to prepare a vaccine. The vaccine was prepared in accordance with the procedures for preparing inactivated FMDV vaccine provided in the section related to veterinary biological products in the "Pharmacopoeia of the People's Republic of China". Each cattle had their tongue subcutaneously injected with 2 mL of the inactivated virus and was continuously observed daily for 6 days. During the observation period, the cattle were in good health, and there were no pathogenic changes or abnormalities in their hoofs, mouths and noses. The experimental cattle were purchased from the FMD non-epidemic area and were detected by the FMD liquid phase blocking ELISA (LPB-ELISA) produced by the National Foot-and-Mouth. Disease Reference Laboratory. The titer of type O FMDV antibodies for each of the cattle was less than 1:4. The FMD non-structural protein 3ABC-ELISA antibody test showed negative results.

9.2 Vaccine Immunity Challenge Test 10 cattle or 10 pigs were immunized with the recombinant type O FMDV vaccine with qualified inspection respectively, and 2 non-immunized controls were set up for each kind of animals respectively; the immune efficacy was determined in each case. The challenge method and the result determination method are all as described in "Manual of diagnostic tests and vaccines for terrestrial animals" (2009 edition, World Animal Health Organization (OIE)).

After 28 days of immunization of pigs, challenge experiments were conducted with the epidemic virus at a 1000-fold median infective dose ($SID_{50}$ dose) for pigs. Continuous observation for 10 days showed that the immunized animals had no visible clinical symptoms and the vaccine can provide 100% protection, as shown in Table 3.

TABLE 3

Clinical symptoms and protection after immunization of pigs with recombinant type O FMDV vaccine

| No. | Immunization dose (mL) | 1 dpc: | 2 dpc: | 3 dpc: | 4 dpc: | 5 dpc: | 6 dpc: | 7 dpc: | 8 dpc: | 9 dpc: | 10 dpc: | Whether can be protected? |
|---|---|---|---|---|---|---|---|---|---|---|---|---|
| 3476 | 2 | 0 | 0 | 0 | 0 | 0 | 0 | 0 | 0 | 0 | 0 | Yes |
| 3483 | 2 | 0 | 0 | 0 | 0 | 0 | 0 | 0 | 0 | 0 | 0 | Yes |

TABLE 3-continued

Clinical symptoms and protection after immunization of pigs with recombinant type O FMDV vaccine

| No. | Immunization dose (mL) | 1 dpc: | 2 dpc: | 3 dpc: | 4 dpc: | 5 dpc: | 6 dpc: | 7 dpc: | 8 dpc: | 9 dpc: | 10 dpc: | Whether can be protected? |
|---|---|---|---|---|---|---|---|---|---|---|---|---|
| 3488 | 2 | 0 | 0 | 0 | 0 | 0 | 0 | 0 | 0 | 0 | 0 | Yes |
| 3492 | 2 | 0 | 0 | 0 | 0 | 0 | 0 | 0 | 0 | 0 | 0 | Yes |
| 3493 | 2 | 0 | 0 | 0 | 0 | 0 | 0 | 0 | 0 | 0 | 0 | Yes |
| 3494 | 2 | 0 | 0 | 0 | 0 | 0 | 0 | 0 | 0 | 0 | 0 | Yes |
| 3495 | 2 | 0 | 0 | 0 | 0 | 0 | 0 | 0 | 0 | 0 | 0 | Yes |
| 3496 | 2 | 0 | 0 | 0 | 0 | 0 | 0 | 0 | 0 | 0 | 0 | Yes |
| 3542 | 2 | 0 | 0 | 0 | 0 | 0 | 0 | 0 | 0 | 0 | 0 | Yes |
| 3543 | 2 | 0 | 0 | 0 | 0 | 0 | 0 | 0 | 0 | 0 | 0 | No |
| 3210 | 0 | 0 | 0 | 1 | 3 | 5 | 5 | 5 | 5 | 5 | 5 | No |
| 3211 | 0 | 0 | 1 | 1 | 3 | 3 | 4 | 4 | 4 | 4 | 4 | No |

Note:
"dpc" represents days post-challenge.

After 28 days of immunization of pigs, challenge experiments were conducted with the epidemic virus at a 10000-fold median infective dose ($BID_{50}$ dose) for cattle. Continuous observation for 10 days showed that the immunized animals had no visible clinical symptoms and the vaccine can provide 100% protection, as shown in Table 4.

TABLE 4

Clinical symptoms and protection after immunization of cattle with recombinant type O FMDV vaccine

| No. | Immunization dose (mL) | 1 dpc | 2 dpc | 3 dpc | 4 dpc | 5 dpc | 6 dpc | 7 dpc | 8 dpc | 9 dpc | 10 dpc | Whether can be protected |
|---|---|---|---|---|---|---|---|---|---|---|---|---|
| 2020 | 2 | 0 | 0 | 0 | 0 | 0 | 0 | 0 | 0 | 0 | 6 | Yes |
| 2021 | 2 | 0 | 0 | 0 | 0 | 0 | 0 | 0 | 0 | 0 | 0 | Yes |
| 2022 | 2 | 0 | 0 | 0 | 0 | 0 | 0 | 0 | 0 | 0 | 0 | Yes |
| 2023 | 2 | 0 | 0 | 0 | 0 | 0 | 0 | 0 | 0 | 0 | 0 | Yes |
| 2024 | 2 | 0 | 0 | 0 | 0 | 0 | 0 | 0 | 0 | 0 | 0 | Yes |
| 2025 | 2 | 0 | 0 | 0 | 0 | 0 | 0 | 0 | 0 | 0 | 0 | Yes |
| 2051 | 2 | 0 | 0 | 0 | 0 | 0 | 0 | 0 | 0 | 0 | 0 | Yes |
| 2052 | 2 | 0 | 0 | 0 | 0 | 0 | 0 | 0 | 0 | 0 | 0 | Yes |
| 2053 | 2 | 0 | 0 | 0 | 0 | 0 | 0 | 0 | 0 | 0 | 0 | Yes |
| 2054 | 2 | 0 | 0 | 0 | 0 | 0 | 0 | 0 | 0 | 0 | 0 | Yes |
| 2055 | 0 | 0 | 1 | 1 | 1 | 2 | 3 | 5 | 5 | 5 | 5 | No |
| 2056 | 0 | 0 | 0 | 1 | 1 | 3 | 3 | 5 | 5 | 5 | 5 | No |

Note:
"dpc" represents days post-challenge.

These results show that the use of this recombinant type O FMDV as a vaccine strain to immunize pigs and cattle, can effectively protect against challenge from the current epidemic type O FMDV.

9.3 Immunity Efficacy of the Vaccine and Cross-Challenge Test

According to the method in "Chinese Veterinary Pharmacopoeia" (2015, edition), the animals used in this experiment were detected by the FMD liquid phase blocking ELISA (LPB-ELISA) produced by the National Foot-and-Mouth. Disease Reference Laboratory and the titer of type O FMDV antibodies for each of the animals was less than 1:4. The FMD non-structural protein 3ABC-ELISA antibody test showed negative results. The animals used in this experiment were strictly kept in ABSL-3 laboratory. According to the 50% protection dose ($PD_{50}$) determination method described in "Chinese Veterinary Pharmacopoeia" (2015, edition), the half-protection dose of the vaccine was determined. The specific method is as follows. There were 15 animals in each immunization group, every 5 of which has a different immunization dose which can be 1 dose per animal, ⅓ dose per animal or ⅑ dose per animal. The animals were immunized respectively. After 28 days, three immunization groups were challenged with the representative epidemic viruses of Mya-98, PanAsia, and Cathay respectively. The challenge dose was 1000-fold $SID_{50}$. Each group had 3 animals as controls and the challenge method was intramuscular injection. After continuous observation for 15 days, according to the symptoms of foot-and-mouth disease such as blisters on lingual surface, gums, and feet, etc, the incidence of disease caused by the virus solution was determined. The case of incidence of disease was determined to be unprotected. The proportion of protected animals in each group was calculated. Finally, according to the Reed-Muench method, $PD_{50}$ was calculated for each group.

The results of immunity efficacy and cross-challenge test showed that the $PD_{50}$ of the recombinant type O FMDV against Mya-98, PanAsia, and Cathay was 13.59, 7.05, and 9.0, respectively. The immune protective efficacy against different topological type O FMDV was higher than the $PD_{50}$ recommended by OIE (>6), indicating that the recombinant type O FMDV is an ideal recombinant anti-type O foot-and-mouth disease vaccine, and can be used for prevention and control of type O FMDV in China and its neighboring countries. See Table 5.

TABLE 5

| Immunity efficacy and cross-challenge protection of recombinant type O FMDV strain | | | | |
|---|---|---|---|---|
| Group No. | Immunization dose | Challenge strain | Protection ratio | $PD_{50}$ |
| Group 1 | 1 | O/BY/CHA/2010 | 5/5 | 13.59 |
| | ⅓ | O/BY/CHA/2010 | 5/5 | |
| | ⅑ | O/BY/CHA/2010 | 4/5 | |
| Control group 1 | 0 | O/BY/CHA/2010 | 0/3 | |
| Group 2 | 1 | O/0834 | 5/5 | 7.05 |
| | ⅓ | O/0834 | 3/5 | |
| | ⅑ | O/0834 | 3/5 | |
| Control group 2 | 0 | O/0834 | 0/3 | |
| Group 3 | 1 | O/0718 | 5/5 | 9.0 |
| | ⅓ | O/0718 | 4/5 | |
| | ⅑ | O/0718 | 3/5 | |
| Control group 3 | 0 | O/0718 | 0/3 | |

Example 10. Preparation of Recombinant Type A FMDV Vaccine and Evaluation of the Immune Effect Thereof 10.1 Vaccine Preparation The recombinant virus rA-FMDV prepared using BHK-21 suspension cells was inactivated with 3 mmol; 1 binary ethylenimine (BEI, Sigma) for 30 h at 30° C., and a blocker sodium thiosulfate solution was added. The mixture was stored overnight at 4° C. for further use. After a safety test, the inactivated antigen was prepared and mixed with ISA 206 adjuvant (SEPPIC, France) in a 1:1 ratio to prepare a vaccine. The vaccine was prepared in accordance with the procedures for preparing inactivated FMDV vaccine provided in the section related to veterinary biological products in the "Pharmacopoeia of the People's Republic of China". Each cattle had their tongue subcutaneously injected with 2 mL of the inactivated virus and was continuously observed daily for 6 days. During the observation period, the cattle were in good health, and there were no visible clinical signs and abnormalities in their hoofs, mouths and noses. The experimental cattle were purchased from the FMD non-epidemic area and were detected by the FMD liquid phase blocking ELISA (LPB-ELISA) produced by the National Foot-and-Mouth Disease Reference Laboratory. The titer of type A FMDV antibodies for each of the cattle was less than 1:4. The FMD non-structural protein 3ABC-ELISA antibody test showed negative results.

10.2 Vaccine Immunity Efficacy Test

The cattle used in this experiment were purchased from FMD non-epidemic area and detected by the FMD liquid phase blocking ELISA (LPB-ELISA) produced by the National Foot-and-Mouth Disease Reference Laboratory and the titer of type A FMDV antibodies for each of the animals was less than 1:4. The FMD non-structural protein 3ABC-ELISA antibody test showed negative results. The animals used in this experiment were strictly kept in ABSL-3 laboratory. The cattle used in this experiment were separated into four groups; one of which is a control group which had been immunized with vaccine prepared from the epidemic strain A/WH/CHA/09, the other three of which are experimental groups which had been immunized with vaccine prepared from the recombinant rA-FMDV, the virus used for challenge was 10000-fold $BID_{50}$ of the epidemic virus A/WH/CHA/09. The challenge method was intradermal injection at several points on lingual surface. After continuous observation for 15 days, according to the symptoms of foot-and-mouth disease such as blisters and ulcers on lingual surface, gums, and feet, etc, the incidence of disease caused by the virus solution was determined. The results of the immune efficacy assay showed that the $PD_{50}$ of the recombinant type A FMDV was between 10.81 and 13.59, while the $PD_{50}$ of the vaccine prepared from the epidemic strain was 5.57 (Table 6).

TABLE 6

| Comparison of $PD_{50}$ of recombinant strain and epidemic strain | | | |
|---|---|---|---|
| Group No. | Immunization dose (mL) | Protection rate | $PD_{50}$ |
| Test 1 | 1 | 5/5 | 10.81 |
| | ⅓ | 5/5 | |
| | ⅑ | 3/5 | |
| | 0 | 0/3 | |
| Test 2 | 1 | 5/5 | 13.59 |
| | ⅓ | 5/5 | |
| | ⅑ | 4/5 | |
| | 0 | 0/3 | |
| Test 3 | 1 | 5/5 | 13.59 |
| | ⅓ | 5/5 | |
| | ⅑ | 4/5 | |
| | 0 | 0/3 | |
| Control group | 1 | 5/5 | 5.57 |
| | ⅓ | 3/5 | |
| | ⅑ | 2/5 | |
| | 0 | 0/3 | |

Example 11. Preparation of Recombinant Bivalent Type O and Type A FMDV Inactivated Vaccine and Evaluation of Immune Effect Thereof 11.1 Vaccine Preparation The recombinant viruses rO-FMDV and rA-FMDV prepared by BHK-21 suspension cells were inactivated with 3 mmol/l binary ethylenimine (BEI, Sigma) for 30 h at 30° C. and a blocker sodium thiosulfate solution was added. The mixture was stored overnight at C for further use. After a safety test, each of the antigens was prepared at a content in which the 146S content is 2.0 μg per cattle (1 mL in total) and each antigen solution was mixed with ISA 206 adjuvant (SEPPIC, France) in a 1:1 ratio to be emulsified in order to prepare a bivalent inactivated vaccine. The vaccine was prepared in accordance with the procedures for preparing inactivated FMDV vaccine provided in the section related to veterinary biological products in the "Pharmacopoeia of the People's Republic of China". For safety test, each cattle had its tongue given intradermal inoculations of 2 mL of the inactivated virus and was continuously observed daily for 6 days. During the observation period, the cattle were in good health, and there were no visible clinical signs and abnormalities in their hoofs, mouths and noses. The experimental cattle were purchased from FMD non-epidemic area and were detected by the FMD liquid phase blocking ELISA (LPB-ELISA) produced by the National Foot-and-Mouth Disease Reference Laboratory. The titer of both type O and type A FMDV antibodies for each of the cattle was less than 1:4. The FMD non-structural protein 3ABC-ELISA antibody test showed negative results.

11.2 Protective Efficacy of Immunization in Animals

The animals which had been screened to be negative were detected by the FMD liquid phase blocking ELISA (LPB-ELISA) produced by the National Foot-and-Mouth Disease Reference Laboratory and the titers of both type O and type A FMDV antibodies for each of the animals were less than 1:4. The FMD non-structural protein 3ABC-ELISA antibody test showed negative results. Pigs were immunized with the obtained recombinant bivalent type O and type A inactivated vaccine which met the safety requirement, meanwhile two pigs were set as non-immunized control in each case, and the immune efficacy was detected in each case. There were 15 pigs in each immunization group, every 5 of which has a different immunization dose which can be 1 dose per animal, ⅓ dose per animal or ⅑ dose per animal. The type O strain used for challenge was Mya-98 strain (O/Mya98/BY/2010) which had been prevalent since 2010, and the type A strain used for challenge was A/GDMM which is a predominant epidemic strain that had been prevalent since 2013. The A/GDMM/2013 strain was deposited with the accession number of FMDV13029 at the CNFMDRL (China National Foot and Mouth Disease Reference Laboratory) designated by Veterinary Bureau of Ministry of Agriculture and Rural Affairs of the People's Republic of China, having an address of NO.1 Xujiaping, Chengguan District, Lanzhou, Gansu Province, China on Mar. 1, 2017. The challenge method and the result determination method were all as described in "Manual of diagnostic tests and vaccines for terrestrial animals" (2009 edition, World Animal Health Organization (OLE)).

After 28 days of immunization, pigs were challenged respectively at a dose of 1000-fold $SID_{50}$. After 15 consecutive days of observation, all of the control pigs had blisters or ulcers on at least one hoof. The case of any occurrence of FMD symptoms on immunized pigs was determined to be unprotected. This experiment was repeated 3 times, and the $PD_{50}$ of the vaccine tested was calculated according to the Reed-Muench method based on the number of protected pigs (Table 7).

TABLE 7

Result of challenge test for immunity efficacy of recombinant bivalent type O and type A FMDV inactivated vaccine

| Batch No. | Challenge strain | 1 dose per animal | ⅓ dose per animal | ⅑ dose per animal | $PD_{50}$ |
|---|---|---|---|---|---|
| Batch 1 | O/MYA98/BY/2010 | 5/5 | 5/5 | 4/5 | 13.59 |
| | A/GDMM/2013 | 5/5 | 5/5 | 5/5 | 15.59 |
| Batch 2 | O/MYA98/BY/2010 | 5/5 | 5/5 | 5/5 | 15.59 |
| | A/GDMM/2013 | 5/5 | 5/5 | 5/5 | 15.59 |
| Batch 3 | O/MYA98/BY/2010 | 5/5 | 5/5 | 5/5 | 15.59 |
| | A/GDMM/2013 | 5/5 | 5/5 | 4/5 | 13.59 |

It can be seen from three times of immunogenicity of the inactivated vaccine experiments, the protective efficacy was greater than the OIE-recommended $PD_{50}$ (ie, 6), indicating that immunization of animals with the recombinant bivalent type O and type A FMDV inactivated vaccine can effectively protect against attacks from the current epidemic strains like type O Mya98 train and type A SEA-97 G2 strain.

11.3 Cross-Protection Test

The same test method as above was used to screen negative animals. Pigs were immunized with the obtained recombinant bivalent type O and type A inactivated vaccine which met the safety requirement. There were 15 pigs in each immunization group, every 5 of which has a different immunization dose which can be 1 dose per animal, ⅓ dose per animal or ⅑ dose per animal. The pigs were immunized respectively. After 28 days, the type O strain used for cross-challenge was PanAsia (O/0834) and Cathay (0718), and the type A strain used for cross-challenge was A/WH/CHA/09 which is an epidemic strain had been prevalent since 2009. The challenge dose was 1000-fold $SID_{50}$, and 3 pigs were used as controls in each group. After continuous observation for 15 days, according to the symptoms of foot-and-mouth disease such as blisters on lingual surface, gums, and feet, etc, the incidence of disease caused by the virus solution was determined. The experiment was repeated for 3 times, and the results of the immune efficacy and cross-protection test showed that the $PD_{50}$ value of the vaccine was greater than 6 in each case, indicating a good protection against cross-challenge. After being immunized with the vaccine, animals can resist the attack of these strains, thus the vaccine can be used as a bivalent vaccine for the prevention of type O and A foot-and-mouth disease. The results are shown in Table 8.

TABLE 8

Results of cross-protection of recombinant type O and type A inactivated vaccine against the challenge of other epidemic FMDV strains

| Batch No. | Challenge strain | 1 dose per animal | ⅓ dose per animal | ⅑ dose per animal | $PD_{50}$ |
|---|---|---|---|---|---|
| Batch 1 | type O PanAsia (08034) | 5/5 | 4/5 | 4/5 | 11.84 |
| | type O Cathay (07018) | 5/5 | 5/5 | 4/5 | 13.59 |
| | type A A/WH/CHA/09 | 5/5 | 5/5 | 5/5 | 15.59 |
| Batch 2 | type O PanAsia (08034 ) | 5/5 | 4/5 | 3/5 | 9.00 |
| | type O Cathay (07018) | 5/5 | 4/5 | 3/5 | 9.00 |
| | type A A/WH/CHA/09 | 5/5 | 5/5 | 4/5 | 13.59 |
| Batch 3 | type O PanAsia (08034) | 5/5 | 4/5 | 3/5 | 9.00 |
| | type O Cathay (07018) | 5/5 | 4/5 | 3/5 | 9.00 |
| | type A A/WH/CHA/09 | 5/5 | 5/5 | 4/5 | 13.59 |

11.4 Duration of Effective Immunity Test

The animals that had been screened to be negative were detected by the FMD liquid phase blocking ELISA (LPB-ELISA) produced by the National Foot-and-Mouth Disease Reference Laboratory and the titers of both type O and type A FMDV antibodies for each of the animals were less than 1:4. The FMD non-structural protein 3ABC-EL1SA antibody test showed negative results. The pigs were vaccinated with the recombinant bivalent type O and type A FMDV inactivated vaccine, which was qualified for safety inspection at 2 mL, dose per pig. On the 7th, 14th, 21st, 28th, 60th, 90th, $120^{th}$, 150th, $180^{th}$, and $210^{th}$ days after immunization, blood serum was collected for antibody detection respectively; meanwhile on the 150th, 180th, and 210th days, the challenge tests were conducted respectively. Each type of antibodies was detected (Table 9, Table 10) and the protection efficacy of the vaccine against viral challenge was recorded (Table 11). The results showed that the vaccine has very good antigen protection and immunogenicity, can effectively stimulate serum to neutralize antibodies, and the duration of immunity s increased to about 6 months (about 4 months for conventional vaccines). It is finally determined that the duration of effective immunity of the recombinant bivalent type O and type A FMDV inactivated vaccine is 6 months.

TABLE 9

ELISA results of type O antibody levels after vaccination

| | Antibody titers | | | | | | | | | |
|---|---|---|---|---|---|---|---|---|---|---|
| Pig No. | Day 7 | Day 14 | Day 21 | Day 28 | Day 60 | Day 90 | Day 120 | Day 150 | Day 180 | Day 210 |
| 106 | 11 | 180 | 180 | >256 | / | / | / | / | | / |
| 107 | 16 | 45 | 90 | 256 | / | / | / | / | / | / |
| 108 | 8 | 45 | 90 | 256 | / | / | / | / | / | / |
| 109 | 22 | 22 | 45 | 180 | / | / | / | / | / | / |
| 110 | 11 | 90 | 180 | >256 | / | / | / | / | / | / |
| 63 | 11 | 22 | 45 | 180 | / | / | / | / | / | / |
| 20 | 11 | 22 | 180 | >256 | / | / | / | / | / | / |
| 36 | >8 | 45 | >256 | >256 | / | / | / | / | / | / |
| 28 | 11 | 90 | 180 | 180 | / | / | / | / | / | / |
| 6 | <8 | 45 | 180 | >256 | / | / | / | / | / | / |
| 1 | 22 | 11 | 90 | >256 | >1024 | >1024 | >1024 | 360 | 128 | / |
| 2 | 11 | 11 | 64 | 90 | 256 | 256 | 128 | 90 | 64 | / |
| 4 | 22 | 90 | 180 | >256 | >1024 | >1024 | >1024 | 360 | 256 | / |
| 5 | <8 | 11 | 32 | 180 | 720 | 720 | 512 | 180 | 128 | / |
| 36 | 11 | 180 | >256 | >256 | >1024 | >1024 | 360 | 128 | 90 | / |
| 7 | <8 | 180 | >256 | >256 | >1024 | >1024 | >1024 | 360 | 256 | / |
| 8 | 22 | >256 | >256 | >256 | >1024 | >1024 | >1024 | 512 | 180 | / |
| 9 | <8 | >256 | >256 | >256 | >1024 | >1024 | 720 | 256 | 128 | / |
| 10 | 45 | 22 | 90 | 90 | 256 | 256 | 90 | 45 | 45 | / |
| 11 | <8 | 22 | 45 | 180 | 180 | 45 | 45 | 32 | <32 | / |
| 12 | 16 | 90 | 180 | 256 | 256 | 128 | 128 | 32 | 45 | / |
| 13 | 11 | >256 | >256 | >256 | >1024 | >1024 | 1024 | 180 | 180 | / |
| 14 | 11 | >256 | >256 | >256 | >1024 | >1024 | >1024 | 256 | 180 | / |
| 15 | 8 | 45 | 64 | >256 | >1024 | >1024 | >1024 | 360 | 256 | / |
| 16 | 32 | 64 | 90 | 256 | 720 | 720 | 256 | 90 | 45 | / |
| 23 | 45 | >256 | >256 | >256 | >1024 | >1024 | 720 | 256 | 180 | / |
| 24 | 16 | 90 | >256 | >256 | >1024 | >1024 | >1024 | 360 | 90 | / |
| 26 | <8 | 22 | 45 | >256 | >1024 | >1024 | 360 | 128 | 180 | / |
| 27 | 11 | >256 | >256 | >256 | >1024 | >1024 | >1024 | 256 | 45 | / |
| 29 | 8 | 45 | >256 | 180 | 512 | 512 | 256 | 90 | 64 | / |
| 31 | 16 | 90 | 180 | >256 | >1024 | >1024 | 512 | 180 | 64 | / |
| 34 | <8 | 22 | 32 | 180 | 360 | 360 | 128 | 90 | 90 | 45 |
| 36 | 32 | 180 | >256 | >256 | >1024 | >1024 | 360 | 256 | 180 | 64 |
| 43 | 11 | 45 | >256 | >256 | >1024 | >1024 | >1024 | 360 | 256 | 90 |
| 45 | <8 | 45 | 64 | 180 | 256 | 256 | 128 | 180 | 90 | 90 |
| 48 | 16 | 180 | >256 | >256 | >1024 | >1024 | 256 | 90 | 45 | <32 |
| 79 | <8 | 180 | >256 | >256 | 720 | 720 | 256 | 128 | 90 | 128 |
| 67 | 11 | 45 | 180 | >256 | 360 | 360 | 180 | 45 | 32 | <32 |
| 65 | 8 | 90 | 90 | >256 | >1024 | >1024 | 720 | 256 | 256 | 256 |
| 64 | 32 | 90 | >256 | >256 | 360 | 256 | 256 | 64 | 64 | 32 |
| 98 | 22 | 45 | 64 | >256 | 720 | 720 | 360 | 256 | 180 | 128 |
| 91 | 45 | >256 | >256 | >256 | >1024 | >1024 | 256 | 128 | 64 | 64 |
| 66 | 8 | 90 | >256 | >256 | 512 | 360 | 360 | 180 | 180 | 180 |
| 60 | 8 | 45 | 64 | 180 | >1024 | >1024 | 720 | 256 | 180 | 90 |
| 78 | 32 | 45 | 90 | >256 | >1024 | >1024 | >1024 | 720 | 256 | 64 |
| 80 | <8 | 22 | 64 | >256 | >1024 | >1024 | 720 | 256 | 180 | 90 |
| 81 | 11 | 22 | 45 | 90 | >1024 | >1024 | >1024 | 360 | 180 | 64 |
| 97 | 22 | 90 | >256 | >256 | >1024 | >1024 | 1024 | 256 | 180 | 45 |
| 95 | <8 | 45 | >256 | >256 | >1024 | >1024 | 360 | 180 | 90 | 64 |
| 88 | 32 | 180 | >256 | >256 | >1024 | >1024 | 720 | 256 | 45 | 45 |
| Percent of pass | 0% | 50% | 86% | 100% | 100% | 97.5% | 97.5% | 87.5% | 80% | 70% |

"/" indicates that the antibody has not been tested (the animal has been challenged)

TABLE 10

| ELISA results of type A antibody levels after vaccination | | | | | | | | | | |
|---|---|---|---|---|---|---|---|---|---|---|
| | Antibody titer | | | | | | | | | |
| Pig No. | Day 7 | Day 14 | Day 21 | Day 28 | Day 60 | Day 90 | Day 120 | Day 150 | Day 180 | Day 210 |
| 106 | 45 | 45 | >256 | 256 | / | / | / | / | / | / |
| 107 | 22 | 90 | >256 | 90 | / | / | / | / | / | / |
| 108 | 45 | 22 | 32 | 180 | / | / | / | / | / | / |
| 109 | 45 | 90 | 180 | 64 | / | / | / | / | / | / |
| 110 | 22 | 45 | 45 | 180 | / | / | / | / | / | / |
| 63 | 11 | 90 | 180 | 90 | / | / | / | / | / | / |
| 20 | 45 | 180 | >256 | 128 | / | / | / | / | / | / |
| 36 | <8 | <8 | 32 | >256 | / | / | / | / | / | / |
| 28 | <8 | 22 | 180 | >256 | / | / | / | / | / | / |
| 6 | 22 | 180 | >256 | 180 | / | / | / | / | / | / |
| 1 | <8 | 22 | 180 | >256 | >1024 | 1024 | 720 | 256 | 90 | / |
| 2 | <8 | 22 | 45 | >256 | >1024 | >1024 | 360 | 128 | 90 | / |
| 4 | 11 | 22 | 128 | >256 | >1024 | >1024 | 360 | 128 | 45 | / |
| 5 | 22 | 45 | 180 | 256 | 720 | 720 | 512 | 256 | 90 | / |
| 36 | 11 | 45 | >256 | >256 | >1024 | >1024 | 360 | 128 | 45 | / |
| 7 | 11 | 11 | 45 | >256 | >1024 | 1024 | 720 | 512 | 180 | / |
| 8 | 45 | 64 | 90 | 128 | 360 | 360 | 256 | 90 | 180 | / |
| 9 | 22 | 90 | >256 | >256 | 512 | 256 | 180 | 64 | 32 | / |
| 10 | 45 | 180 | >256 | >256 | >1024 | >1024 | 1024 | 720 | 180 | / |
| 11 | 22 | 45 | 180 | 256 | >1024 | 1024 | 720 | 360 | 128 | / |
| 12 | 22 | 45 | >256 | >256 | 512 | 512 | 180 | 45 | 32 | / |
| 13 | 22 | 11 | 45 | >256 | >1024 | >1024 | 256 | 180 | 90 | / |
| 14 | 45 | 11 | 180 | >256 | 128 | 256 | 128 | 45 | 45 | / |
| 15 | 11 | 22 | 45 | 128 | 90 | 128 | 90 | 45 | 45 | / |
| 16 | 11 | 22 | 180 | 256 | >1024 | >1024 | 360 | 90 | 180 | / |
| 23 | <8 | 45 | 45 | 180 | >1024 | >1024 | 256 | 180 | 45 | / |
| 24 | 11 | 90 | >256 | >256 | 720 | 720 | 360 | 128 | 90 | / |
| 26 | <8 | 11 | 32 | >256 | >1024 | 1024 | 256 | 256 | 180 | / |
| 27 | 22 | 32 | 128 | >256 | >1024 | >1024 | 256 | 90 | 64 | / |
| 29 | 11 | 11 | 45 | 128 | 128 | 256 | 128 | 64 | 64 | / |
| 31 | 22 | 90 | >256 | >256 | 360 | 360 | 180 | 90 | 90 | / |
| 34 | 22 | 45 | >256 | >256 | >1024 | >1024 | 720 | 128 | 128 | 90 |
| 36 | 90 | 180 | 180 | >256 | 720 | 720 | 256 | 180 | 90 | 64 |
| 43 | <8 | 32 | >256 | >256 | >1024 | >1024 | 1024 | 256 | 180 | 45 |
| 45 | 11 | 45 | >256 | >256 | >1024 | >1024 | 720 | 128 | 90 | 90 |
| 48 | <8 | 45 | 180 | >256 | 720 | 512 | 180 | 128 | 128 | 64 |
| 79 | 11 | 11 | 180 | 180 | >256 | >256 | 256 | 64 | 1:180 | 1/90 |
| 67 | 1/8 | 45 | 180 | 90 | 180 | 180 | 180 | 180 | 64 | 45 |
| 65 | <8 | 45 | >256 | >256 | 360 | 360 | 180 | 256 | 180 | 90 |
| 64 | 11 | 45 | >256 | >256 | >1024 | 1024 | 720 | 360 | 128 | 64 |
| 98 | 11 | 22 | 45 | 45 | 32 | <32 | <32 | <32 | <32 | <32 |
| 91 | 11 | 180 | 180 | >256 | 720 | 512 | 360 | 90 | 90 | 180 |
| 66 | <8 | 32 | >256 | >256 | 720 | 720 | 512 | 180 | 64 | 32 |
| 60 | 22 | 45 | 64 | 180 | 360 | 256 | 128 | 64 | 45 | 32 |
| 78 | 11 | 32 | >256 | >256 | 360 | 360 | 360 | 128 | 90 | 45 |
| 80 | 11 | 45 | >256 | >256 | >1024 | >1024 | 720 | 360 | 128 | 90 |
| 81 | 11 | 22 | 180 | >256 | 720 | 720 | 720 | 256 | 90 | 128 |
| 97 | 45 | 22 | >256 | >256 | >1024 | >1024 | 1024 | 360 | 180 | 90 |
| 95 | <8 | 45 | 180 | 256 | >1024 | 1024 | 360 | 128 | 256 | 180 |
| 88 | <8 | 90 | 180 | >256 | >1024 | >1024 | 720 | 360 | 45 | 45 |
| Qualified rate | 2% | 26% | 78% | 98% | 97.5% | 97.5% | 97.5% | 90% | 75% | 65% |

"/" indicates that the antibody has not been tested (the animal has been challenged)

On the 7th, the 14th, the 21st, the 28th, the 60th, the 90th, the 120th, the 150th, the 180th, and the 210th days after immunization, the blood was collected to separate serum for type O and type A antibody detection. The antibody level turned positive on the 7th day after immunization, the antibody qualified rate on the 14th day could reach 26% or more, the antibody qualified rate on the 21st day reached 78% or more, the antibody qualified rate on the 28th day could reach 98% or more, and the antibody level on the 60th, the 90th, and the 120th days was in a stable state. The antibody level on the 150th day began to decline, the antibody qualified rate on the 180th day could still reach 75% or more, and that on the 210th day could reach 65% or more.

TABLE 11

| Protection rate against challenge on the 28th, 180th, and 210th days after immunization | | | |
|---|---|---|---|
| Challenge strain | Day 28 | Day 180 | Day 210 |
| O/MYA98/BY/2010 | 100% | 90% | 70% |
| A/GDMM/2013 | 100% | 80% | 80% |

The challenge tests were conducted on the 28th, 180th, and 210th days after immunization. The protection rate against challenge by each serotype FMDV strain on the 28th and 180th day after immunization in each case was not less than 80%. The protection rate against challenge by each serotype FMDV strain on the 210th day after immunization in each case reached up to 70%.

According to analysis of the results of the 7-month challenge protection rate and the measured antibody titer, the recombinant type O and type A FMDV bivalent inactivated vaccines has good immunity protection, and its duration of immunity can be elevated to 6 months, which greatly increases the immunogenicity of the type O and type A FMDV vaccines.

The above-described embodiments merely illustrate the embodiments of the present disclosure, and the description thereof is relatively specific and detailed, but it should not be read to limit the scope of the disclosure. It should be pointed out that those skilled in the art can make other improvements without departing from the conception of the present disclosure, and these are all within the protection scope of the present disclosure. Therefore, the scope of protection of the present disclosure shall be defined by the appended claims.

The invention claimed is:

1. A bivalent foot-and-mouth disease virus (FMDV) vaccine composition comprising a first FMDV vaccine and a second FMDV vaccine, the first FMDV vaccine comprising a first FMDV which contains or is encoded by first recombinant FMDV nucleic acids, the sequence of the first recombinant FMDV nucleic acids comprises a nucleic acid sequence of a FMDV O/CHA/99 strain, but in the nucleic acid sequence of the FMDV O/CHA/99 strain, 177 consecutive nucleotides in the L gene connected with P1 gene, all of the P1 gene, and 1206 consecutive nucleotides in the P2 gene connected with the P1 gene are replaced as a whole by a sequence shown in SEQ ID NO: 1 in a nucleic acid sequence of the O/JSCZ/2013 strain; the second FMDV vaccine is a recombinant type A FMDV strain, which comprises a nucleic acid sequence shown in SEQ ID NO:4.

2. The vaccine composition according to claim 1, wherein the first FMDV vaccine is capable of stimulating immune response to protect against challenge from a type 0 FMDV strain.

3. The vaccine composition according to claim 2, wherein the type 0 FMDV strain is an epidemic strain of Mya-98, PanAsia, or Cathay lineage.

4. The vaccine composition according to claim 3, wherein the type 0 FMDV strain is O/BY/CHA/2010, O/0834 or O/0718 strain, and the $PD_{50}$ value of the first FMDV vaccine against O/BY/CHA/2010, O/0834 or O/0718 strain in each case is greater than 6.

5. The vaccine composition according to claim 1, wherein the second FMDV vaccine is capable of stimulating immune response to protect against challenge from a type A FMDV strain.

6. The vaccine composition according to claim 5, wherein the type A FMDV strain is SEA-97 G1 or SEA-97 G2 strain.

7. The vaccine composition according to claim 6, wherein the type A FMDV strain is A/WH/CHA/09 or A/GDMM/2013 strain, and the $PD_{50}$ value of the second FMDV vaccine against A/WH/CHA/09 or A/GDMM/2013 strain in each case is greater than 6.

8. The vaccine composition according to claim 1, wherein there is no immunosuppression between the first FMDV vaccine and the second FMDV vaccine.

9. A method of preparing a vaccine composition as claimed in claim 1, comprising the steps of:

(a) cultivating a first FMDV vaccine strain and collecting the first FMDV vaccine strain;

(b) cultivating a second FMDV vaccine strain and collecting the second FMDV vaccine strain;

(c) inactivating the first FMDV vaccine strain collected in step (a) and the second FMDV vaccine strain collected in step (b) and then mixing both.

10. The method according to claim 9, wherein the FMDV vaccine strains are emulsified after the mixing in the step (c).

11. The method according to claim 10, wherein the emulsification is performed with ISA 206 adjuvant in a volume ratio of 1:1.

12. The method according to claim 9, wherein the first FMDV vaccine strain and the second FMDV vaccine strain are adapted to suspension cell culture.

13. The method according to claim 9, wherein the mixing is performed by mixing the first FMDV vaccine strain and the second FMDV vaccine strain in a 1:1 ratio of antigen content.

14. A method for preventing and/or controlling foot-and-mouth disease in animals comprising administering the FMDV vaccine composition according to claim 1 to the animals.

* * * * *